United States Patent
Bhethanabotla et al.

(10) Patent No.: US 11,828,726 B2
(45) Date of Patent: Nov. 28, 2023

(54) PORTABLE ORTHOGONAL SURFACE ACOUSTIC WAVE SENSOR SYSTEM FOR SIMULTANEOUS SENSING, REMOVAL OF NONSPECIFICALLY BOUND PROTEINS AND MIXING

(71) Applicant: UNIVERSITY OF SOUTH FLORIDA, Tampa, FL (US)

(72) Inventors: Venkat R. Bhethanabotla, Tampa, FL (US); Shuangming Li, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 17/986,884

(22) Filed: Nov. 14, 2022

(65) Prior Publication Data

US 2023/0070329 A1    Mar. 9, 2023

Related U.S. Application Data

(63) Continuation of application No. 16/691,588, filed on Nov. 21, 2019, now Pat. No. 11,499,943.

(60) Provisional application No. 62/770,670, filed on Nov. 21, 2018.

(51) Int. Cl.
| | |
|---|---|
| *G01N 29/04* | (2006.01) |
| *G01N 29/12* | (2006.01) |
| *G01N 33/483* | (2006.01) |
| *G01N 33/68* | (2006.01) |

(52) U.S. Cl.
CPC .......... *G01N 29/041* (2013.01); *G01N 29/12* (2013.01); *G01N 33/4833* (2013.01); *G01N 33/6803* (2013.01)

(58) Field of Classification Search
CPC .. G01N 29/041; G01N 29/12; G01N 33/4833; G01N 33/6803; G01N 2291/012; G01N 2291/0255; G01N 2291/0256; G01N 2291/0423; G01N 29/022; G01N 29/036
See application file for complete search history.

(56) References Cited

U.S. PATENT DOCUMENTS

| | | | |
|---|---|---|---|
| 7,878,063 B1 * | 2/2011 | Cular | G01N 29/024 73/61.79 |
| 8,018,121 B1 | 9/2011 | Cular | |
| 11,499,943 B1 * | 11/2022 | Bhethanabotla | G01N 29/12 |
| 2017/0168026 A1 | 6/2017 | Morton et al. | |

OTHER PUBLICATIONS

Cular et al., Removal of Nonspecifically Bound Proteins on Microarrays Using Surface Acoustic Waves, IEEE Sensors Journal, 2008, 8(3):314-320.

(Continued)

*Primary Examiner* — Tarun Sinha
(74) *Attorney, Agent, or Firm* — QUARLES & BRADY LLP

(57) ABSTRACT

Disclose herein is a portable platform based on a direct digital synthesizer (DDS) is investigated for the orthogonal SAW sensor, integrating signal synthesis, gain control, phase/amplitude measurement, and data processing in a small, portable electronic system. The disclosed platform allows for simultaneous removal of non-specific binding proteins, and mixing, as well as improved incubation time.

22 Claims, 17 Drawing Sheets

(56) References Cited

OTHER PUBLICATIONS

Sankaranarayanan et al., Acoustic Streaming Induced Elimination of Nonspecifically Bound Proteins from a Surface Acoustic Wave Biosensor: Mechanism Prediction Using Fluid-Structure Interaction Models, Journal of Applied Physics, 2010, 108:104507, pp. 1-11.
Sankaranarayanan et al., Flow Induced by Acoustic Streaming on Surface-Acoustic-Wave Devices and its Application in Biofouling Removal: A Computational Study and Comparisons Io Experiment, Physical Review E, 2008,177:066308, pp. 1-19.
Singh et al., Orthogonal Surface Acoustic Wave Device Based on Langasile for Simultaneous Biosensing and Biofouling Removal, Applied Physics Letters, 2009, 94(26):263503, pp. 1-3.

* cited by examiner

PORTABLE ORTHOGONAL SURFACE ACOUSTIC WAVE SENSOR SYSTEM FOR SIMULTANEOUS SENSING, REMOVAL OF NONSPECIFICALLY BOUND PROTEINS AND MIXING

CROSS-REFERENCE TO RELATED APPLICATION

This application claims the benefit of and priority to U.S. Provisional Patent Application No. 62/770,670, entitled "PORTABLE ORTHOGONAL SURFACE ACOUSTIC WAVE SENSOR SYSTEM FOR SIMULTANEOUS SENSING, REMOVAL OF NONSPECIFICALLY BOUND PROTEINS AND MIXING," filed on Nov. 21, 2018, the contents of which are hereby incorporated by reference in its entirety herein.

BACKGROUND

There has been a great deal of interest in developing acoustic-wave-based devices for biological sensing. Surface acoustic wave (SAW) devices with shear horizontal (SH) wave propagation are leaders for liquid-phase applications due to their highly-sensitive velocity and attenuation responses to perturbations from mass loading. A guided SH-SAW device, with a waveguide layer on the delay path, could reduce the power consumption and enhance the sensitivity of the sensor. Owing to its high sensitivity, low cost, and ease of integration with an electrical circuit, the guided SH-SAW biosensor has huge potential in point-of-care testing when integrated with a portable measurement system.

But issues related to the non-specific binding (NSB) of interfering proteins and incubation times impede the possibility of real-time monitoring at point-of-care using portable biosensor systems. In applications demanding low limits of detection in the pg/mL range, such as for cancer biomarkers, enhancements using nanoscale physics are necessary to quantify these biomarker concentrations. However, the highly-sensitive SAW biosensors used for such applications are susceptible to background noise caused by the nonspecific adsorption of other proteins when used on a real sample such as a drop of blood. This interference from NSB proteins to the sensor signal, and long incubation times present serious challenges to achieving SAW-based point-of-care (POC) testing systems.

A system for sensing and removal of NSB proteins simultaneously for POC applications is therefore desirable.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1A:
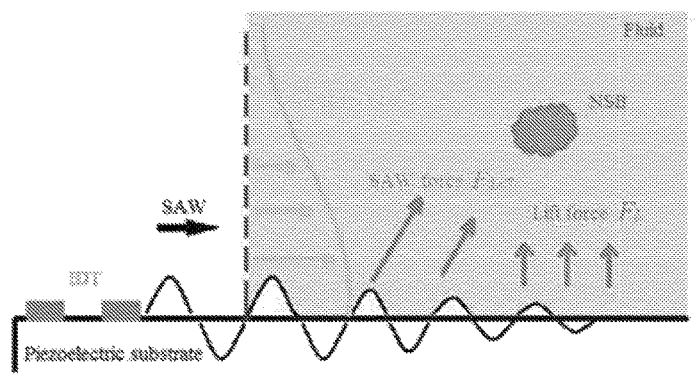
FIG. 1A depicts an example of a schematic diagram of NSB protein removal using acoustic streaming forces generated by the Rayleigh wave device.

As described above, it would be desirable to have a system and method for simultaneously sensing analyte proteins in a sample while also removing the nonspecifically bound proteins from the sample. Disclosed herein are examples of portable systems for orthogonal SAW devices capable of measuring a sensor signal and removing NSB protein interference. In some embodiments, a portable platform based on a direct digital synthesizer (DDS) can be used for the orthogonal SAW sensor, which can integrate signal synthesis, gain control, phase/amplitude measurement, and data processing in a small, portable electronic system.

In the following disclosure, various specific embodiments are described. It is to be understood that those embodiments are example implementations of the disclosed inventions and that alternative embodiments are possible. All such embodiments are intended to fall within the scope of this disclosure.

Acoustic Streaming

Surface acoustic wave streaming can be used to decrease nonspecific adsorption, as well as improve incubation time and sample fluid-mixing. Rayleigh waves with a prominent surface normal component can selectively remove NSB proteins from the surfaces of biosensors. Rayleigh waves can also enable fluid-mixing of a sample. Acoustic streaming is typically generated using Rayleigh SAWs.

Recently, we introduced a SAW device in ST quartz capable of propagating Rayleigh and surface skimming bulk (SSBW) waves in orthogonal directions. With a suitable wave-guide bringing the energy of the SSBWs to the surface, this device has the potential for simultaneously reducing NSB protein interference and incubation times using acoustic streaming from the Rayleigh waves, while allowing for liquid phase quantification of biomarkers from the liquid phase using the wave-guided SSBWs. Device configurations that can use a wave guide to bring the SSBWs to the surface, thus further enhancing sensitivity, are possible within this orthogonal configuration.

However, there is a challenge in utilizing these and other SAW devices in POC applications. SAW devices are usually operated in the MHz to GHz range, thus vector network analyzer (VNA) is commonly used for signal measurement. While it can provide accurate parameter testing and monitoring, the VNA is very large and expensive. In addition, for the driving signal for NSB removal, a power-controllable, variable frequency signal generator is essential, but such signal generator equipment is also very heavy and expensive.

Current measurement methods for a SAW sensor system based on this device require large-size and expensive equipment such as a VNA, signal generator, and frequency counter, which are not suitable for portable, especially point-of-care, applications.

Orthogonal SAW Sensor

Biological sensors can be prone to difficulties with binding of desired proteins. This has been recognized as one of the most challenging issues found in protein patterning of biosensors. To address this problem, chemical techniques and processes have been developed, such as self-assembled monolayers (SAMs), blocking layers and zwitterionic polymers.

Compared with these traditional methods, however, SAW streaming can enable less sample processing and easier surface modifications. As shown in FIG. 1A, the interaction of Rayleigh waves with a fluid medium results in a wave mode conversion to leaky SAWs. These leaky SAWs propagate along the boundary between the piezoelectric solid and liquid media and excite longitudinal waves into the fluid at the Rayleigh angle θ. Direct SAW forces result in the initial NSB particle detachment, whereas hydrodynamic forces (drag and lift) prevent their reattachment. As the NSB forces caused by weak interactive forces (i.e., Van der Waals and hydrophobic) are typically much weaker than the specific binding forces between antibodies and antigens, the wave streaming can remove only the NSB proteins without detaching the specific antibody-antigen links with a modest energy input. Acoustic wave streaming with Rayleigh waves can also enable fluid-mixing and faster incubation times.

Figure 1B:
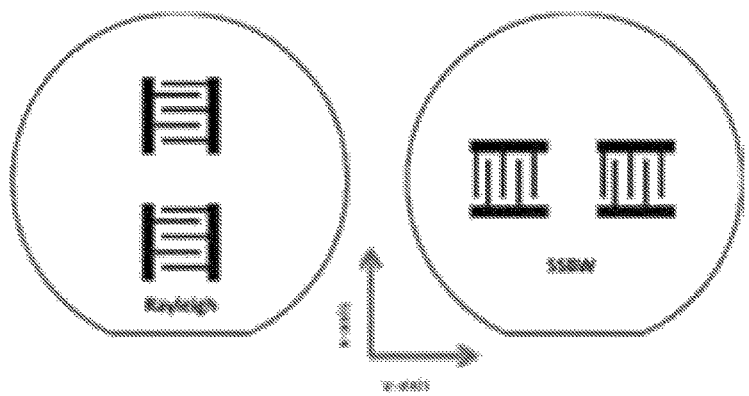
FIG. 1B depicts an example of different wave modes in the orthogonal device in ST quartz.

While Rayleigh waves are useful for generating acoustic streaming forces for mixing and NSB protein removal, they are unsuitable for biosensing in liquid media. For this, shear-horizontal (SH) polarization is used to avoid damping the wave. ST quartz can support Rayleigh and SSBWs with SH polarization in orthogonal directions, as shown in FIG. 1B. With the application of a wave guide, the SSBWs can be converted to Love waves, providing for a sensitive biosensing platform.

Waves of different character can propagate along the two orthogonal propagation directions. In one direction, the waves are shear horizontal waves, and in the other, they can be Rayleigh or a mixture of waves with mostly shear vertical polarization. In ST quartz and in langasite, two different waves are possible in the two orthogonal directions. Shear horizontal waves can propagate along one direction that can be suited for biosensing. Mixed shear-vertical (langasite) or pure Rayleigh (ST-Quartz) waves can propagate along a direction orthogonal to the shear horizontal waves that can be suited for biofouling removal.

A device propagating Rayleigh waves (or a mixture of shear vertical waves) and shear horizontal surface acoustic waves in orthogonal directions fabricated in ST quartz or langasite can achieve simultaneous detection and nonspecific binding (NSB) protein removal. The disclosed orthogonal device, which produces SH waves in one direction and either pure Rayleigh or a mixture of shear vertical waves in the other orthogonal direction, can be realizable in at least ST quartz and langasite. Thus, the orthogonal SAW device described herein can be capable of simultaneous NSB removal and sensing, along with mixing and improved incubation time.

Figure 1C:
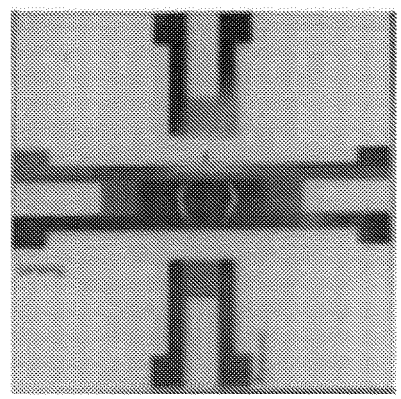
FIG. 1C depicts an example of an orthogonal surface acoustic wave chip.

As shown in FIG. 1C, the dual function SAW sensor was realized by placing two pairs of interdigital transducer (IDT) electrodes on the same ST-quartz substrate. To obtain a guided wave, a gold layer is added along the delay path of the sensing direction. An O-ring cell was fabricated on the center of the chip as the sensing area utilizing SU-8 photoresist.

The orthogonal SAW devices were fabricated on 4 inch, 0.5 mm thickness, and single-side polished ST X quartz wafers. Each of the IDT electrodes for the sensing and removal directions consisted of 60 finger pairs with an electrode width of 10 μm and wavelength of 40 μm. The delay path for the sensing direction is of 8 mm length and 2 mm width, which is coated with a 100 nm gold film as a waveguide layer. No reflecting gratings were applied in this work and it is a specific set-up design for biotesting application with an O-ring cell.

These patterns were fabricated by the following steps: First, NR9 1500PY (Futurrex) negative photoresist was applied by spin coating on the wafer after solvent cleaning. After the pre-bake, the coated wafer was exposed to broadband UV light using an EVG-make mask aligner, followed by a hard bake. The pattern was developed in RD6 (Futurrex) developer for 12 s, followed by rinsing with DI water and drying with nitrogen gas. E-beam evaporation was used to deposit 20 nm/100 nm Ti/Au adhesion and metal layers. The deposition rate was set to 0.5 nm/s for Ti deposition and 1 nm/s for Au to obtain strong adhesion between the substrate and metal layer. An acetone bath was used to lift-off the metal and the remaining metal pieces were removed with solvent cleaning, with ultrasonication used as needed to achieve complete cleaning. After the metal patterns were fabricated, the wafer was spin-coated with SU-8

50 negative photoresist for a similar lithography process, to obtain an O-ring cell of 2 mm diameter and approximately 100 micron height. The patterned wafers were diced into 25×25 mm individual chips.

Portable System Design

Two methods can be used for measuring the SAW device response. One is frequency detection. This basic testing system consists of an RF amplifier for a feedback loop and a frequency counter. The electronic circuit should satisfy the Barkhausen stability criterion: (1) The loop gain is equal to unity in absolute magnitude, that is, $|\beta A|=1$; and (2) the phase shift around the loop is zero or an integer multiple of $2n$, that is, entire phase shift=$2\pi n$ ($n=0, \pm 1, \pm 2, \ldots$), upon which, the entire circuit would oscillate as a resonator around the center frequency of the SAW device.

Though this method only requires a relatively simple circuit design, it is not stable and can be affected by the environment, which usually causes frequency hopping. As there could be many frequency points that satisfy the oscillation starting conditions, once the SAW is affected by a big perturbation, the circuit will self-oscillate at a different frequency. In addition, this system also requires a high-speed frequency counter that is not easily miniaturized for portable application.

The other method is phase detection using a phase detector, comparing the input/output difference of the SAW device. The system gets an RF source with a certain frequency and splits the signal two ways, one passes through the SAW device and the output signal is compared with the other signal. The phase difference as a voltage output can be easily measured by a voltmeter. Since it is not based on feedback, this detection system is not susceptible to frequency hopping and would be very stable.

However, to achieve simultaneous sensing and NSB removal, an RF signal source for both the sensing and removal inputs can be applied. Direct digital synthesis (DDS) could produce an analog waveform by utilizing a time-varying signal in a digital form and converting using a digital-to-analog converter (DAC). It can offer fast switching of frequency, a wide output bandwidth, and very high-frequency resolution. Thus, a DDS-based system with time division multiplexing for this dual function sensor system is described herein.

The disclosed system and associated methods are designed do both sensing of analyte proteins in a fluid while also removing the nonspecifically bound proteins from the sample, which interfere with the sensing by adding to the signal. The system can remove using the Rayleigh (or the mixture) of waves that are shear vertical. To do this, the Rayleigh or mixed waves are generated at higher and higher intensities to remove the non-specifically bound proteins.

The electronics are also used to sense specifically bound proteins by measuring the phase shift in the shear horizontal waves in the orthogonal direction to the above Rayleigh (or mixed shear vertical) waves. Analyte proteins (cancer markers such as CEA or PSA) will bind to antigens that are already attached to the surface in the middle region between the 4 sets of interdigital transducers arranged in a square. Then, the nonspecifically bound proteins can be removed using the Rayleigh waves. After this, the shear horizontal waves are excited, and the phase is measured across that set of IDTs. The change in phase compared to when the analyte proteins are not bound to the antibodies on the surface (before exposure to blood with CEA or PSA) is proportional to the concentration of this analyte CEA or PSA. This way, cancer markers in the blood can be quantified or sensed.

Figure 2A:
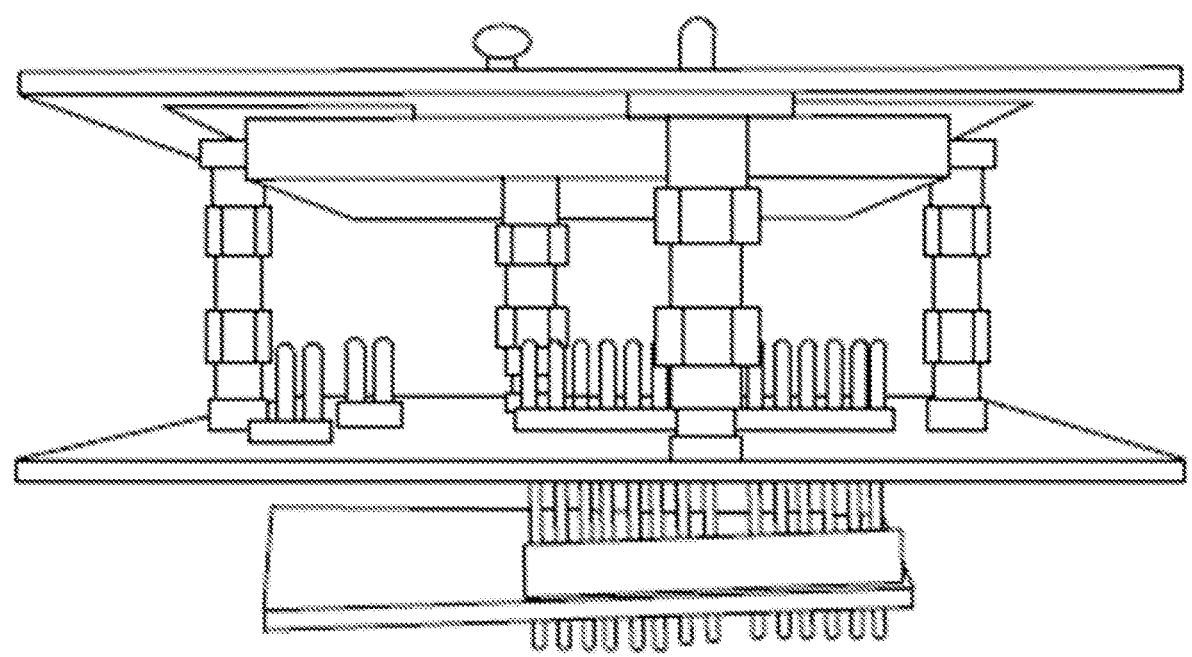
FIGS. 2A-2B depict an example of an electronic circuit system comprising three boads assembled as a portable instrument.
Figure 2B:
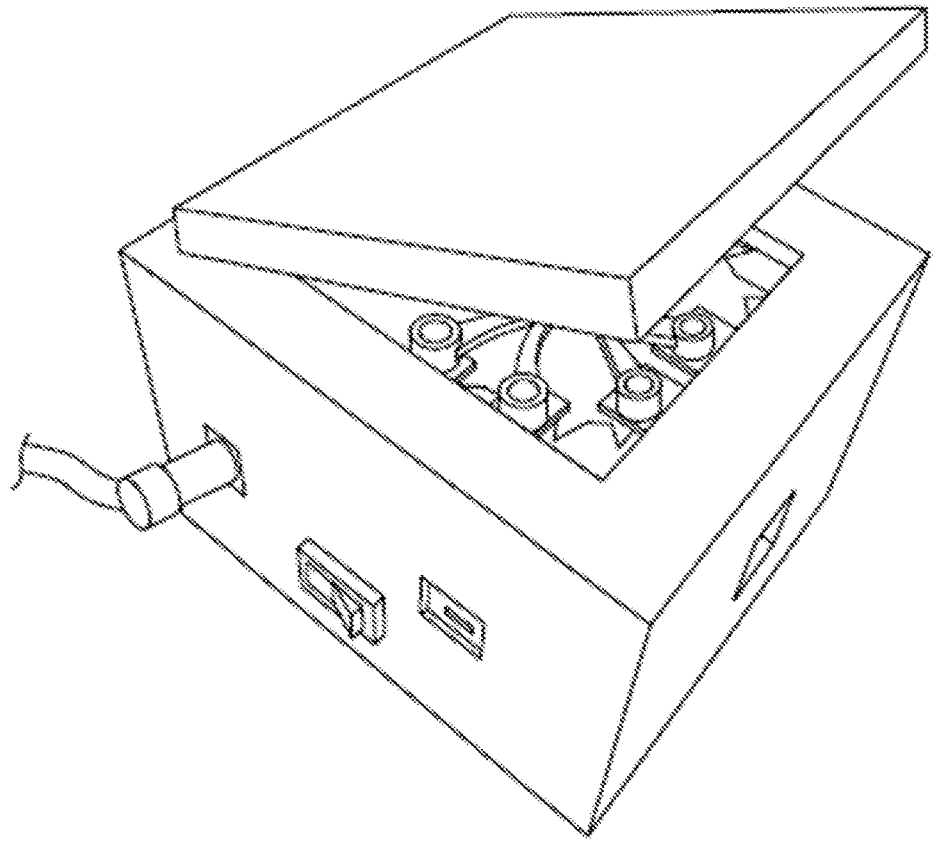

The electronic circuit system can comprise three boards and is assembled as a portable instrument, as shown in FIGS. 2A and 2B. The bottom layer can provide the microcontroller for the main program operating the system. It can provide serial communication with the local computer and the control with other IC chips. The middle layer, which can be the main circuit board, is designed for the power supply, DDS signal generation, signal processing, and data acquisition/converting, etc. The top layer can be a specially designed PCB board as a chip holder for the SAW device with connecting clips and buffer circuit.

To realize a real portable system, some peripheral designs can added to the system. The power supply of this system can range from 7-12 V. Communication between the portable prototype and computer can be via USB cable. The data communication, storage, processing and displaying can be conducted with the self-developed SAW sensor data monitoring software. The SAW device can be loaded on a specially designed board with eight clips touching with each electro pad of the SAW sensor. This board can be connected with the main circuit board via SubMiniature version A (SMA) connectors of 50Ω impedance. In addition, these electronics can housed in a 3D printed shell package. The dimensions of the portable device are 110×110×80 mm.

Figure 3:
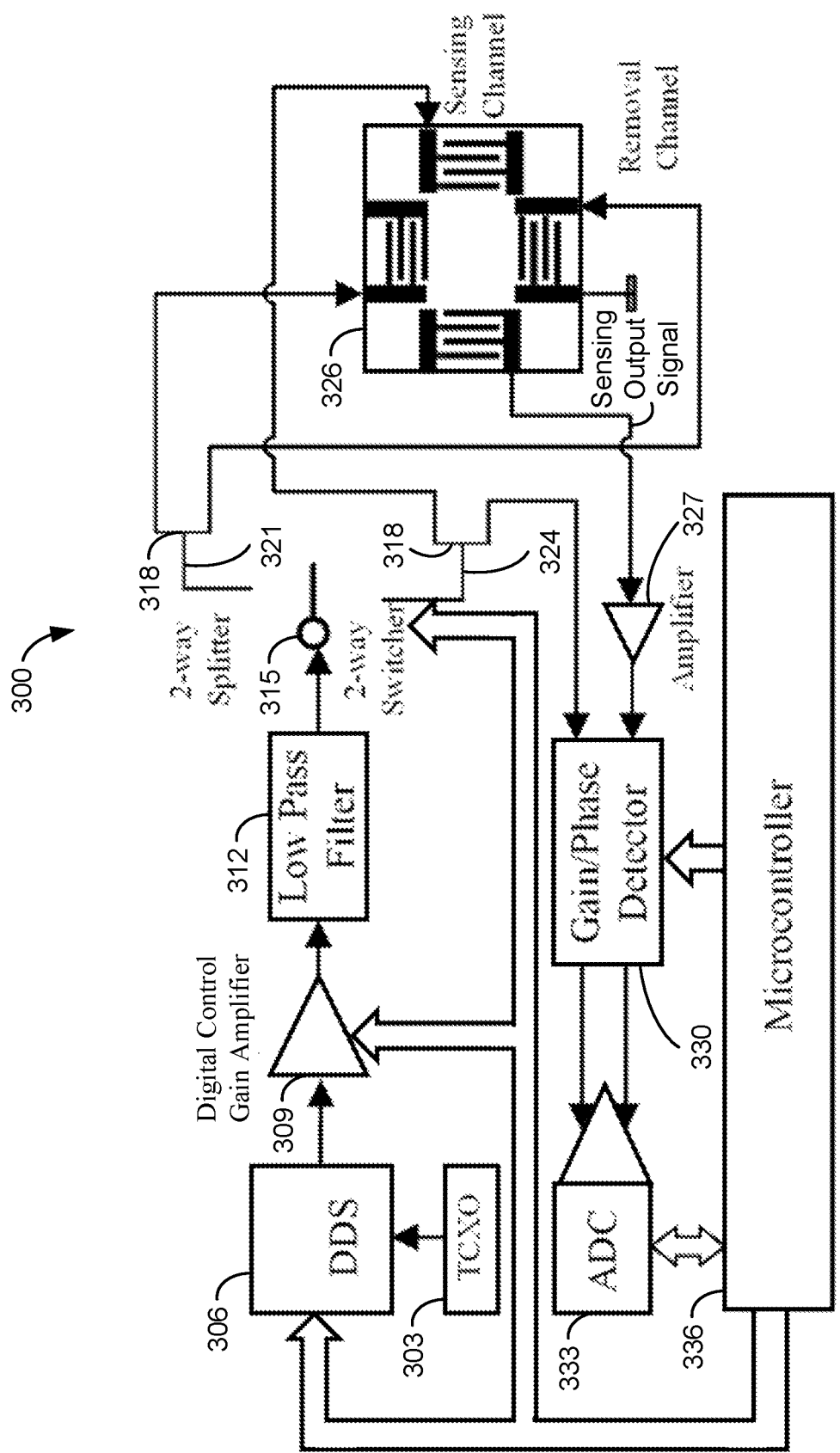
FIG. 3 depicts an example of a schematic block diagram of a direct-digital-synthesizer-based orthogonal surface acoustic wave system.

FIG. 3 shows an embodiment of an electronic system to measure phase, transmission loss, and frequency for the SAW sensor device. An RF signal can be generated from the DDS chip 306 with a frequency that can be set by the microcontroller. In some embodiments, the RF signal can take the form of a sine wave. For example, an RF signal can be generated from the 32-bit DDS chip 306 and the working frequency can be calculated and set by the microcontroller. This synthesizer can offer high resolution of 0.233 Hz and a wide bandwidth sine wave up to 400 MHz with special designed temperature compensated crystal oscillator (TCXO) 303. TCXO 303 can provide a stand frequency signal to the DDS 306. For example, the TCXO 303 can provide a stable reference with frequency stability of 0.5 ppm at 1 GHz, which can be eligible for biotesting at room temperature. In some embodiments, the DDS 306 can generate the RF signal based on the stand frequency received from the DDS 306.

The RF signal can be amplified by a digital controlled variable gain amplifier (DVGA) 309. The DVGA 309 can, for example, an provide a +19 dB gain, with final output power about +16.4 dBm. The internal-integrated digital controlled attenuator of this amplifier can provide a power attenuation coefficient ranging from 0 dB to −31.5 dB (the final gain is from −12.5 dB to +19 dB), as another example. The RF signal can be filtered by a low pass filter 312.

The RF signal can be delivered into two channels 321, 324 controlled by an RF switcher 315. In some embodiments, after amplification and low-pass filtering, the RF signal can be delivered into two channels 321, 324 controlled by two-way RF switcher 315, according to the purpose of use. A removal channel 321 channel can be separated into two paths by a two-way 0° power splitter 318 and used to load the two sides of the removal IDTs. A sensing channel 324 channel can be separated into two paths by the power splitter 318. In some embodiments, one signal can be sent to the SAW sensing device 326 as the input signal for sensing. In some embodiments, the other signal can be sent as one input source of a gain/phase detector 330 as a reference signal.

The output signal of the SAW device 326, as another input source, can be compared with the reference signal via the gain/phase detector 330. The output voltage of the gain/ phase detector 330, as a function of the two input signals' amplitude/phase differences, can represent an insertion loss and phase shift of the SAW device 326. The voltage value can be obtained by a microcontroller 336 via an analog-to-digital converter (ADC) 333. In some embodiments, the ADC 333 can be a 12-bit ADC, which can offer a phase angle shift resolution of 0.044° and insertion loss shift of 0.0147 dB, respectively. Data can be received from the microcontroller 336 by a computing device based on processing and calculations using the output voltage.

Figure 4:
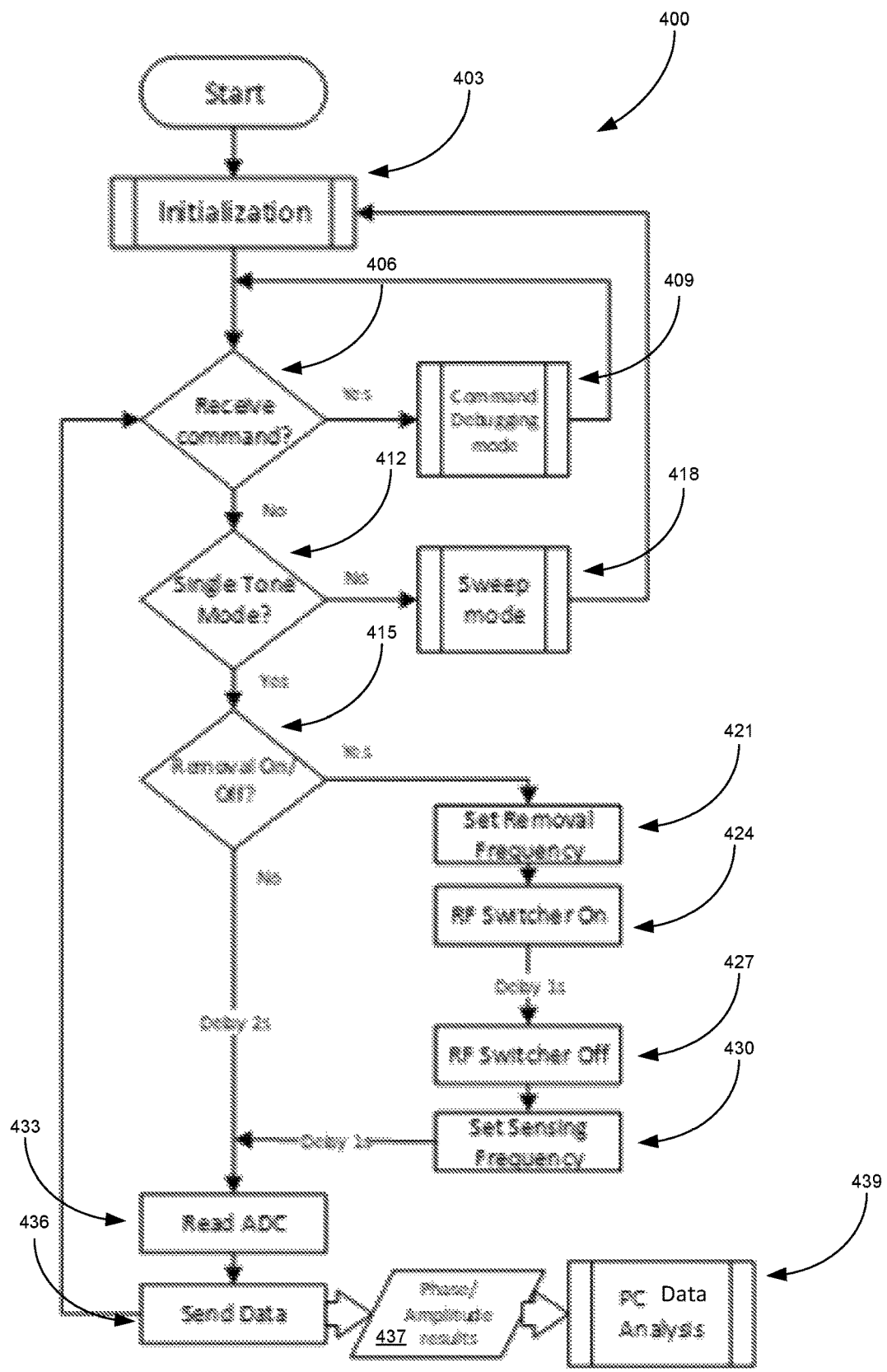
FIG. 4 depicts an example of a flow diagram of a surface acoustic wave sensing and removal process of the direct-digital-synthesizer-based orthogonal surface acoustic wave system depicted in FIG. 3.

FIG. 4 is a flow chart of an SAW sensing and removal process 400 of the system 300 of FIG. 3. The process 400 can start with an initialization subprocess 403, where several parameters are set. Next, the system 300 can determine at step 406 whether it received a command code from the computing device. If so, the process 400 can proceed to command debugging mode 409. If not, the process 400 can proceed to step 412 to determine whether the system 300 is in a single tone mode. If not, the process 400 can proceed to a sweep mode subprocess 418. Otherwise, the system 300 can run in a single tone mode. Next, system 300 can determine at step 415 whether a removal mode of the system 300 should be switched on or off. If the removal mode should be switched off, the process 400 can proceed to step 421. Otherwise the process 400 can proceed to step 433. At step 421, the system 300 can set the removal frequency and turn on the RF switcher 315 at step 424. After a 1-second delay, RF switcher 315 can be turned off at step 427 and the system 300 can set the sensing frequency. After a 1 second delay, the ADC 333 results can be read by the microcontroller 336. If the removal mode is off, it can run with delay 2 seconds and the ADC results can be read at step 433. At step 436, the results which contain the information of the current phase/amplitude results can be sent to computer for future data analysis subprocess. The process 400 can then proceed back to step 406.

Figure 5:
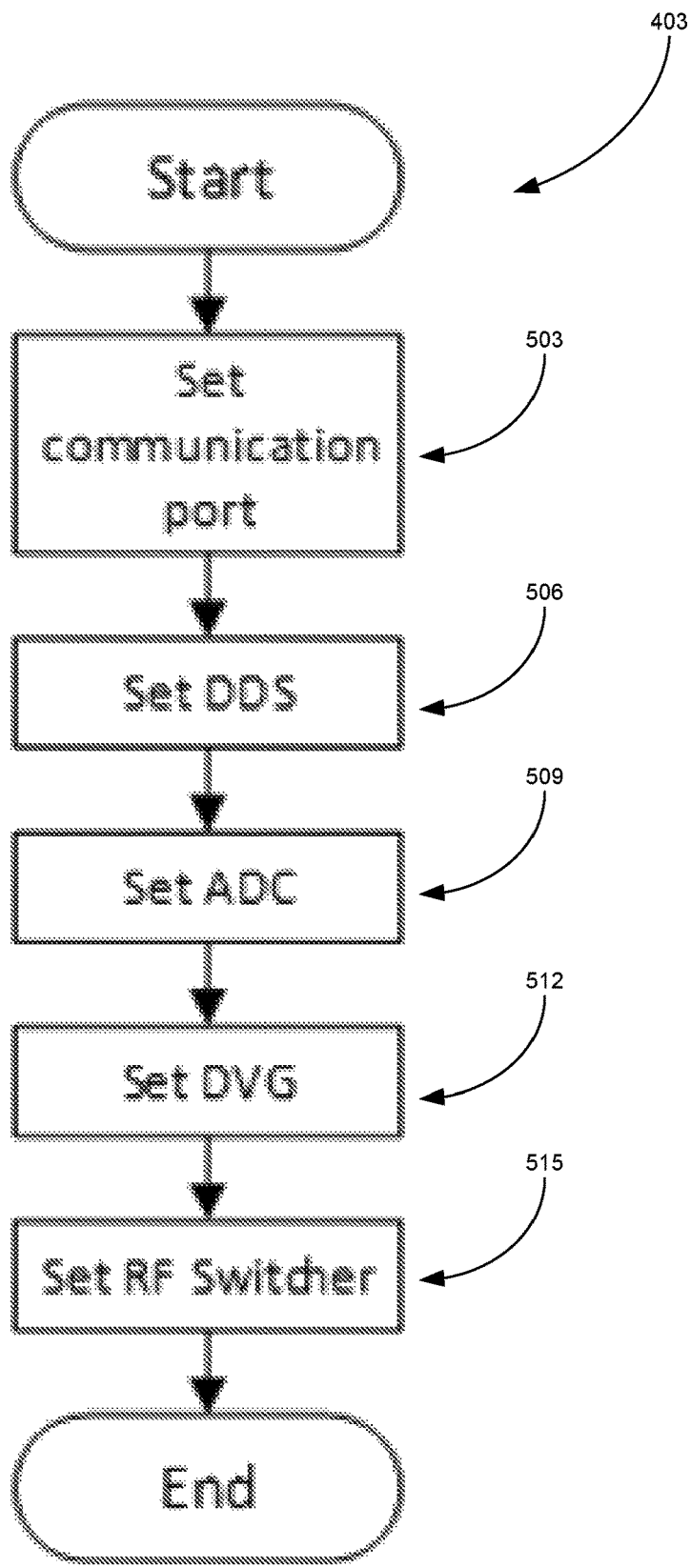
FIG. 5 depicts an example of a flow diagram of an initialization subprocess of the direct-digital-synthesizer-based orthogonal surface acoustic wave system depicted in FIG. 3.

FIG. 5 is a flow chart of an initialization subprocess 403 of the process 400 in FIG. 4. First, the system 300 can set the communication port such as SPI, serial port, input/output pins, and wire bus at step 503. Next, at step 506 the DDS 306 can be set. The sensing frequency and removal frequency can be set. The default output signal can be a sensing frequency. At step 509, the ADC 333 channels and configurations can be set. At step 512, the digital controlled gain amplifier 309 can be set. Then, the RF switcher 315 can be set to off as default. The subprocess 403 can then return to main process 300. The ADC 33 can be initialized by a default setting on Channel set up and a command can switch which ADC 333 channel works. DVGA 309 can be initialized by a default setting on its gain factor, and a command can change the gain factor of DVGA 309. The ADC 333 can be initialized by the default setting on Channel set up and a command can switch which ADC 333 channel works. DVGA 309 can be initialized by a default setting on its gain factor, and command can change the gain factor of the DVGA 309.

Figure 6:
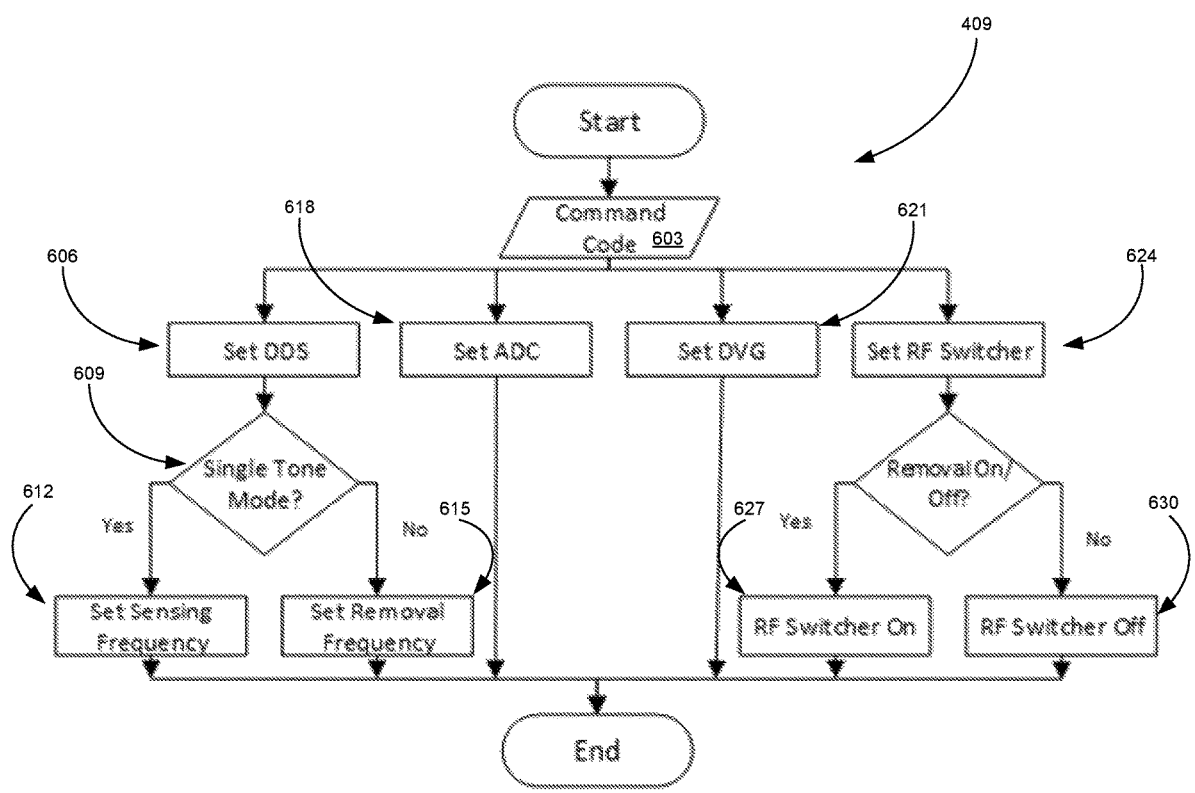
FIG. 6 depicts an example of a flow diagram of a command debugging mode subprocess of the direct-digital-synthesizer-based orthogonal surface acoustic wave system depicted in FIG. 3.

FIG. 6 is a flow chart of command debugging mode subprocess 409 of the process 400 in FIG. 4. The subprocess 409 can start with a command code 603 checking. The subprocess 409 can switch to different a subprocess: Set DDS 606, Set ADC 618, Set DVG 621 and Set RF Switcher 624. In the Set DDS subprocess 606, the system 300 can determine whether it is in a single tone mode. If yes, the microcontroller 336 can set the sensing frequency to the DDS 306, and if no, the microcontroller 336 can set the removal frequency. In RF Switcher subprocess 624, the system 300 can if removal mode is no. If yes, the RF switcher 315 can be turned on. Otherwise, the RF switcher 315 is off. Then after setting, the process can return to the process 400.

Figure 7:
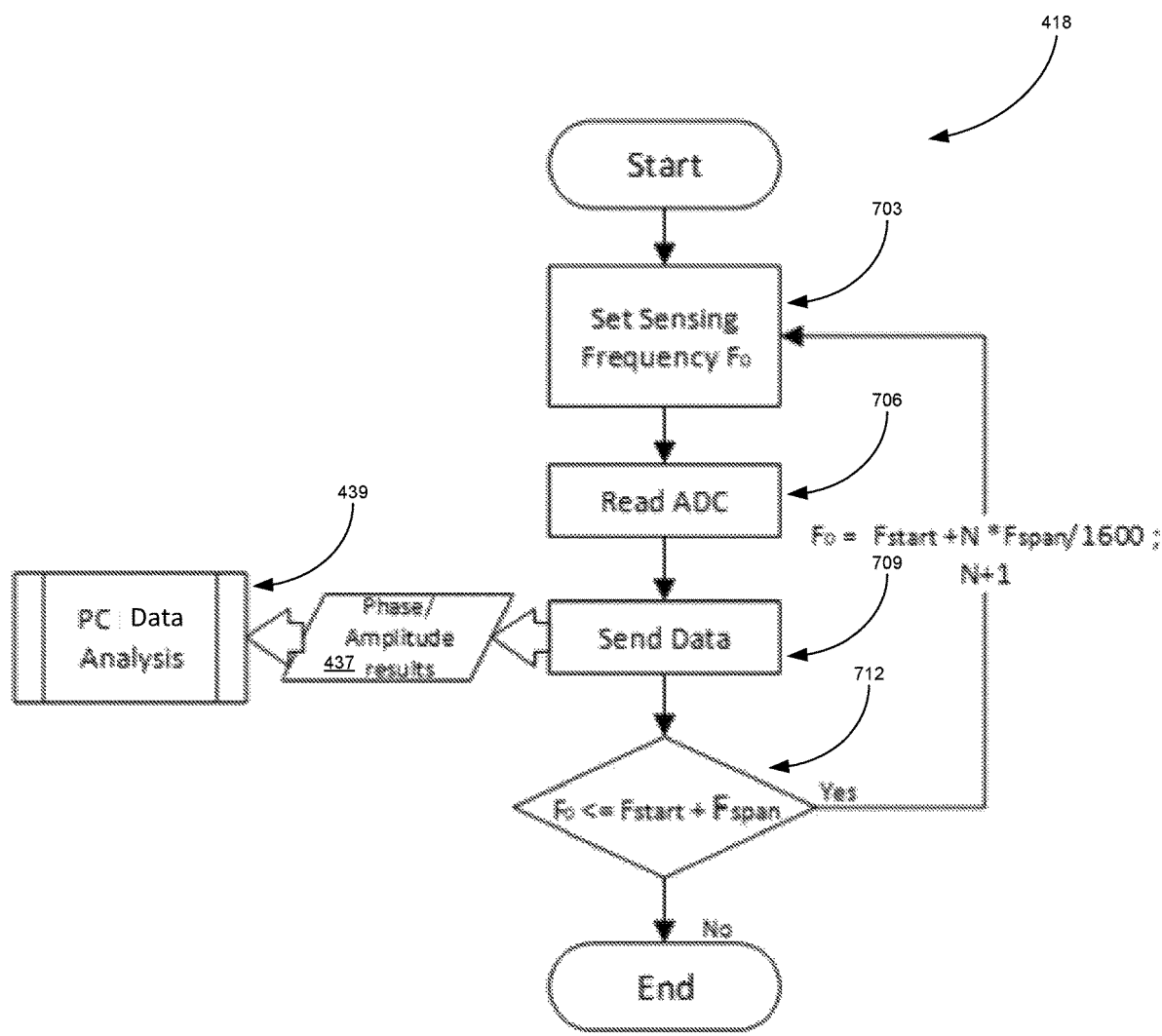
FIG. 7 depicts an example of a flow diagram of a sweep mode subprocess of the direct-digital-synthesizer-based orthogonal surface acoustic wave system depicted in FIG. 3.

FIG. 7 is a flow chart of sweep mode subprocess 418 of the process 400 in FIG. 4. The system 300 can first set the DDS sensing frequency to the start frequency $f_{start}$ beginning from $f_0$. Next, microcontroller 336 can read the ADC 333 and obtain the phase/amplitude results 437. The data can be sent to a computing device and can be analyzed with PC data analysis process 439. Next in step 712, the current set frequency $f_0$ can be compared with a final frequency $f_{final}$, which is equal to adding start frequency and span frequency $f_{final}=f_{start}+f_{span}$. If the current set frequency is not larger than the final frequency, the set frequency is given by $f_0=f_{start}+n*f_{span}/1600$. n is the counter of the current loop number. Then the subprocess 418 can return to step 703 with updated $f_0$. If the current set frequency $f_0$ is larger than the final frequency $f_{final}$, the subprocess 418 can end and return to the process 400.

Figure 8:
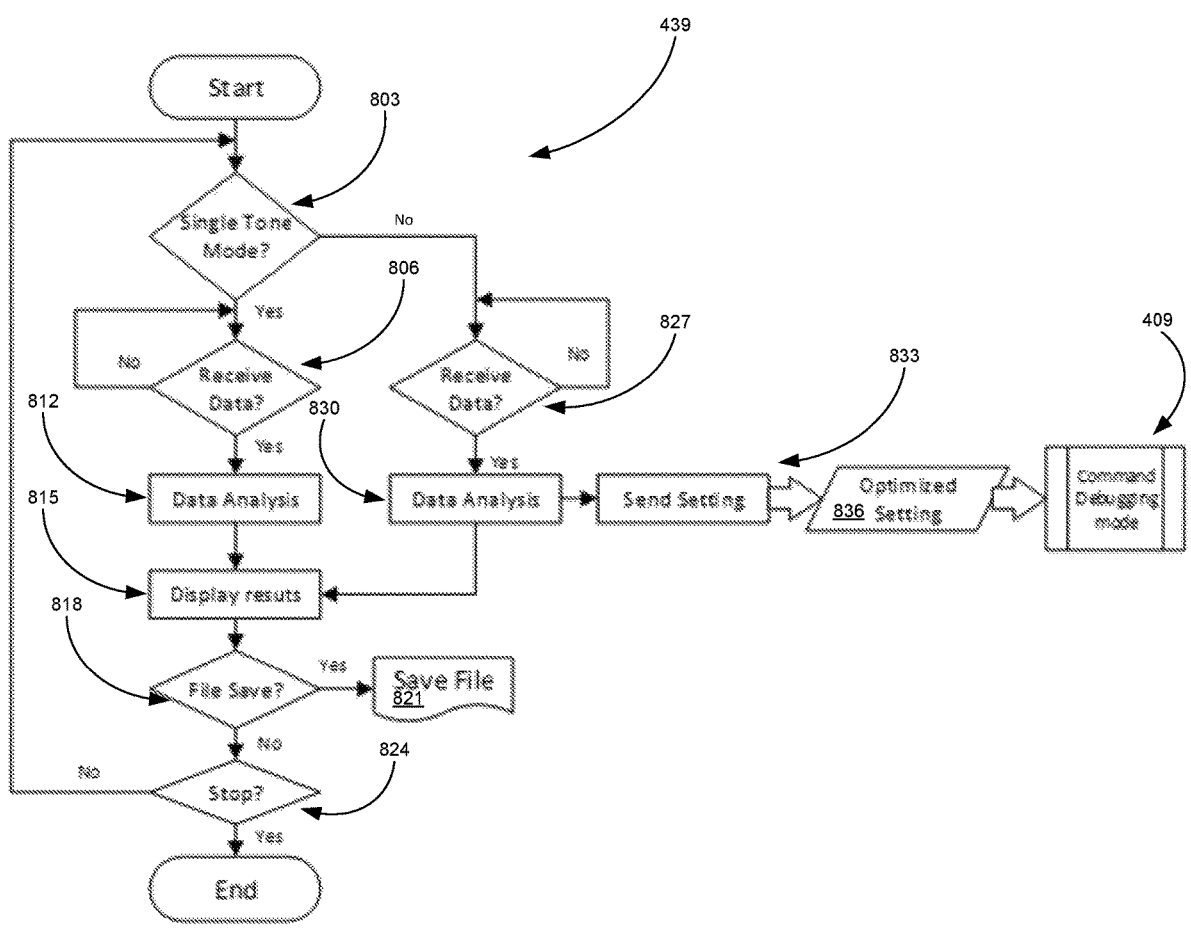
FIG. 8 depicts an example of a flow diagram of a PC data analysis program associated with the direct-digital-synthesizer-based orthogonal surface acoustic wave system depicted in FIG. 3.

FIG. 8 is a flow chart of PC data analysis process 439. The PC data analysis program 439 can operate in the computing device. First, the process 439 can determine whether the system 300 is in single tone mode. If not, the process 439 can run as follows. First, the process 439 can check whether any data are received. If not, the process 439 can keep checking. If the data are received, the system 300 can analyze the data to obtain a center frequency of the SAW chips and send the optimized setting back to the system 300 as a command code so that the device system 300 can run in the command mode. If the system 300 is in single tone mode, the process can run as follows. First, the process 400 can check whether any data are received. If not, the process can continue to check. Once the data are received, the data can be calculated in data analysis step 812 and displayed on a display in the display results step 815. Then, the computing device can determine whether the file needs to be saved at step 818. If yes, the file can be saved 821 to the computing device. If not, the process 439 can return to step 809 for another loop, until the computing device stops the process.

Experimentation

The surface of the SAW device was solvent cleaned and treated by $O_2$ plasma. A surface modification based on a SAM and carbodiimide chemistry was employed. Gold-coated disks were modified by thiols. The gold waveguide layer was incubated for 2 hours with 10 mM MUA in pure ethyl alcohol, then rinsed with pure ethyl alcohol and dried by $N_2$ gas. The activation solution (200 mM EDC and 50 mM NHS in deionized water) was then added to activate the carboxyl group for 10 min at room temperature. Then, protein A was assembled on the surface of the SAW device and stored overnight, followed by 200 μg/mL rabbit IgG with the same procedure. Then, 1% BSA solution in PBS was used to block the non-sensing surface (treatment time at least two hours), then rinsed with PBS solution and dried using $N_2$ gas. This modified SAW biosensor was stored at 4° C.

Figure 9:
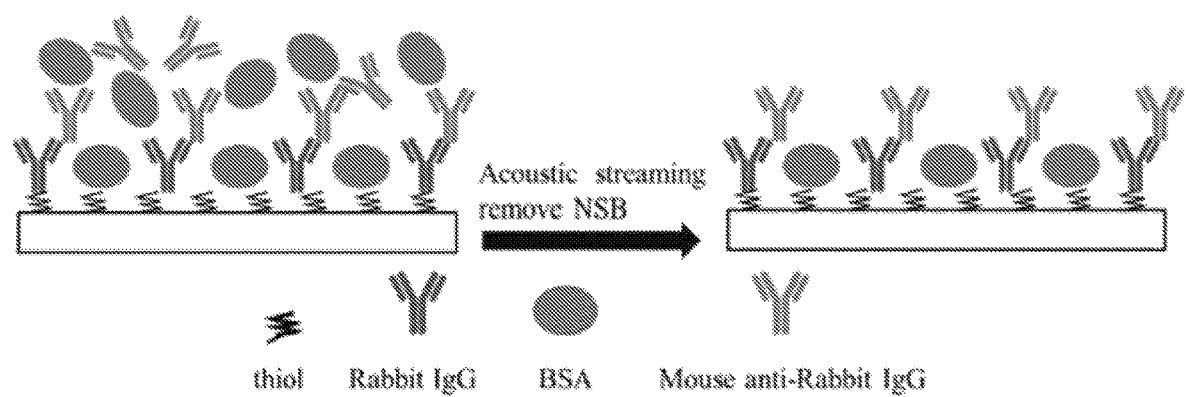
FIG. 9 depicts an example of a schematic of a surface acoustic wave sensing and nonspecific binding removal strategy.

The modified SAW chip was tested for IgG sensing as followed, as shown in FIG. 9. First, the system was set working in sensing mode, and removal channel frequency was set on its center frequency. The phase shift was monitored. 10 μL PBS solution was added in the O ring cell to obtain the baseline. After drawing up the PBS solution, 10 μL mouse anti-rabbit IgG of 10 μg/mL was added. Once the phase shift became stable, a 10 μL solution of 10 mg/mL BSA in PBS was added as the nonspecific proteins. After the phase shift became stable again, the removal RF power was switched on to separate the nonspecifically bounded proteins from the surface, then removal power was turned off.

Figure 10A:
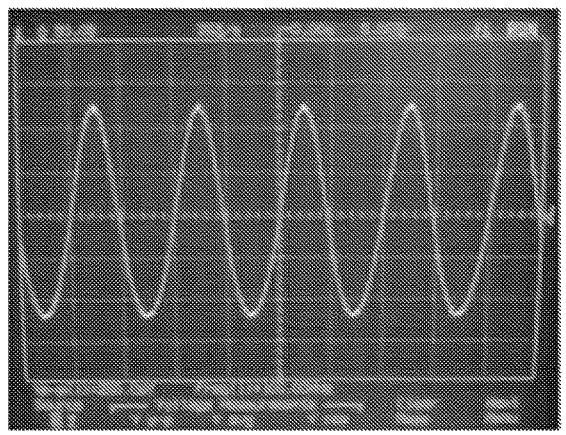
FIG. 10A depicts an example of oscilloscope measurement results at 100 MHz with a digital gain amplifier power attenuation coefficient of 15 dB.
Figure 10B:
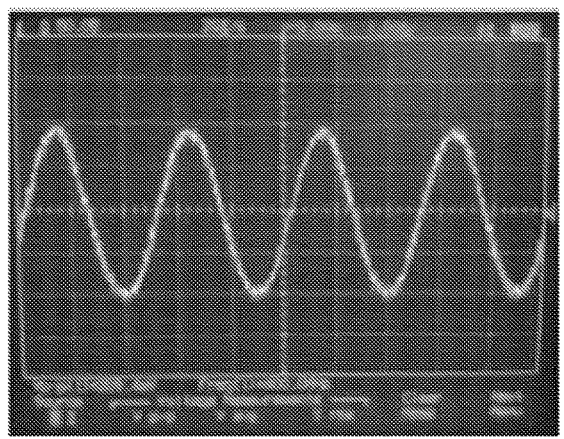
FIG. 10B depicts an example of oscilloscope measurement results at 400 MHz with a digital gain amplifier power attenuation coefficient of 15 dB.
Figure 10C:
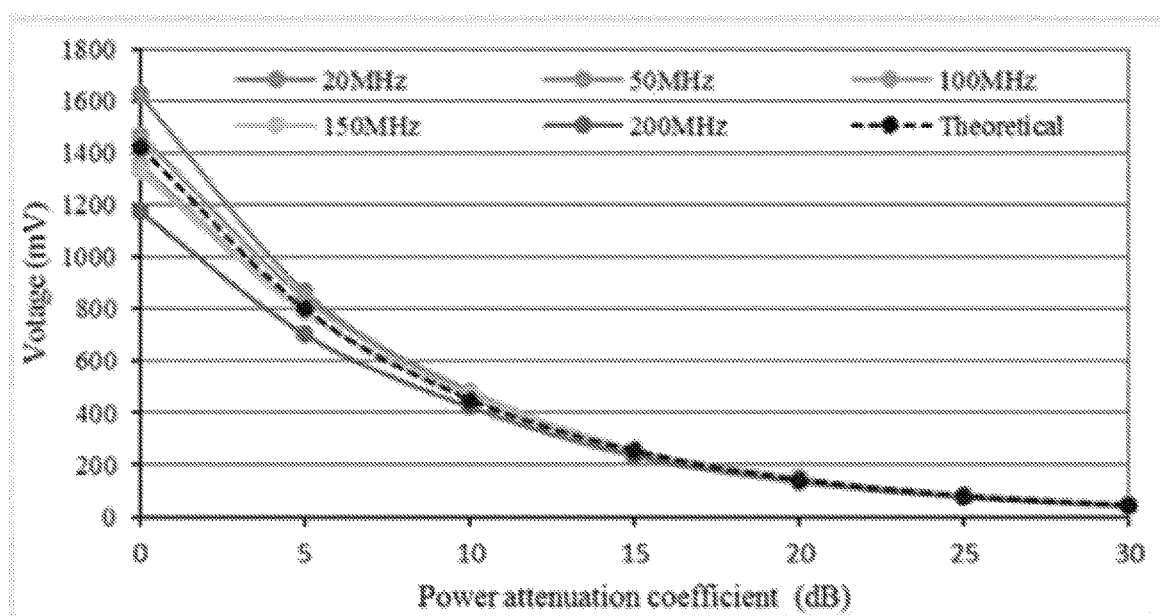
FIG. 10C depicts an example of a line chat showing output voltage in different frequencies vs. a power attenuation coefficient of a digital gain amplifier.

The DDS system output performance was evaluated using Agilent 54616B oscilloscope, to measure the output sine wave signal frequency and voltage. The output port of the DDS system was connected to the oscilloscope via a 50Ω cable. FIGS. 10A and 10B show the DSS output signals at 100 MHZ and 400 MHz after amplified, and the DDS system can synthesize very stable sine waves.

The system was tested for a range from 20 MHz to 200 MHz, at various power levels by adjusting the power attenuation coefficient of the digital gain amplifier. It shows that the output voltage can have a slight drop with increasing frequency. The output voltage can also decrease when increasing the power attenuation coefficient of digital gain amplifier. The decreasing trend matches the setting power damping ratio (dB), according to the theoretical calculation rule between voltage gain and power gain.

Figure 11A:
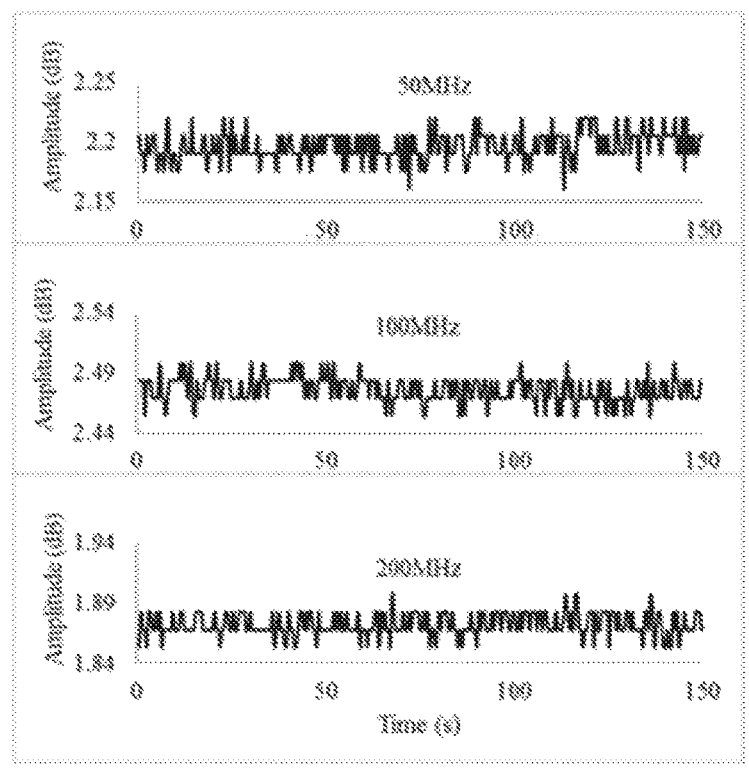
FIGS. 11A-11B depict examples of a circuit stability test at different frequencies for amplitude and phase angle.
Figure 11B:
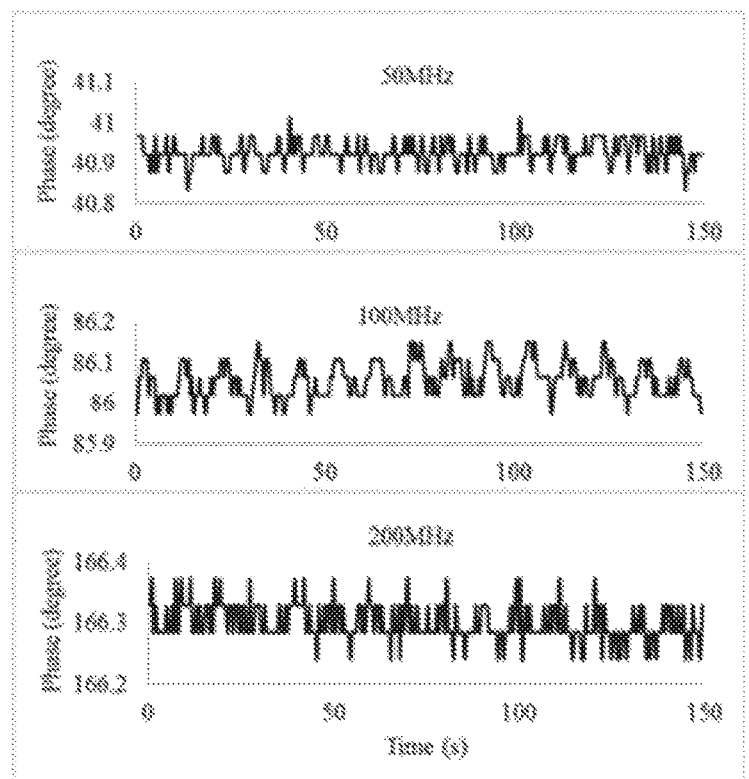

The circuit without the influence of SAW device was tested for 10 min (sampling rate of 0.5 Hz) to assess the system stability, as shown in FIGS. 11A and 11B. The SAW sensing channel was electronically shorted using the 50Ω cable. The DDS output frequency was tested at 50 MHz, 100 MHz, and 200 MHz, respectively. The ADC results only vary within 1-2 least significant bit (LSB), corresponding to lower than 0.088 degree/0.0293 dB in phase angle/amplitude, which indicates that the designed circuit can have excellent stability.

Figure 12A:
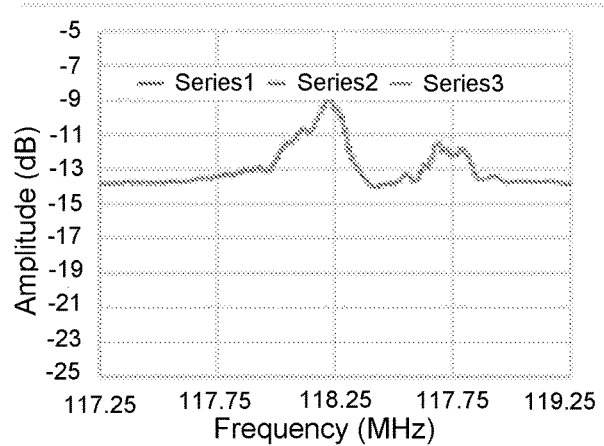
FIG. 12A-12D depict examples of comparisons of amplitude vs. frequency results for a portable system with a vector network analyzer.
Figure 12B:
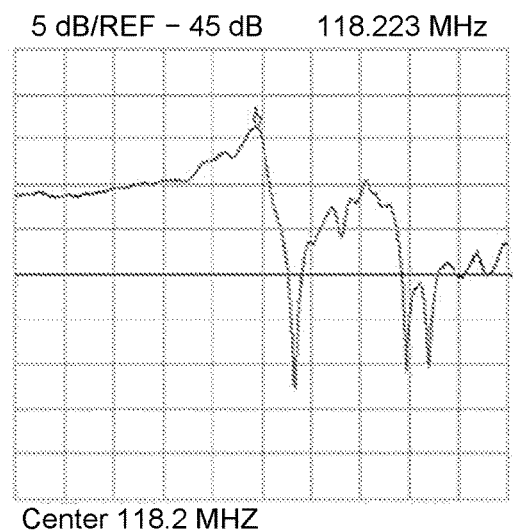
Figure 12C:
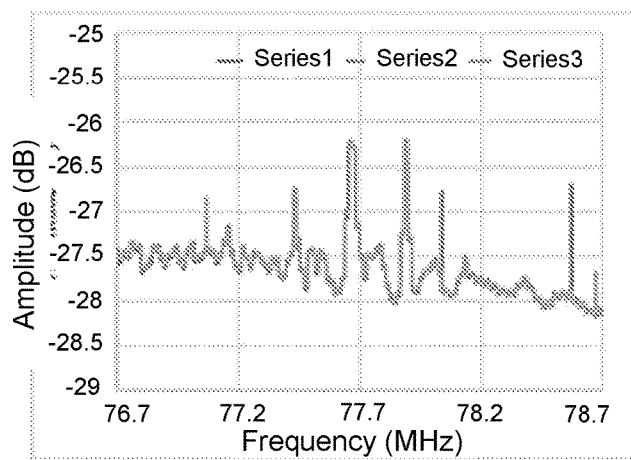
Figure 12D:
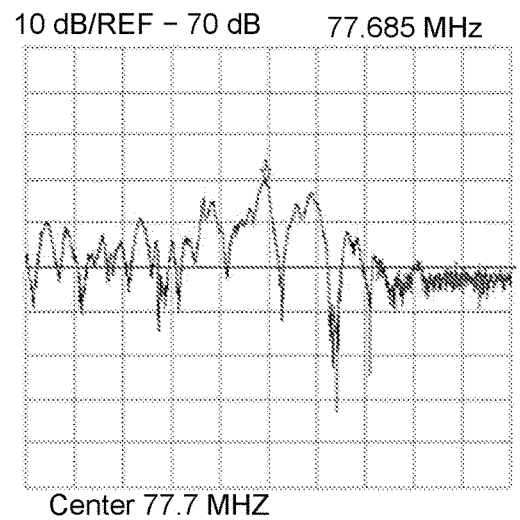
Figure 17A:
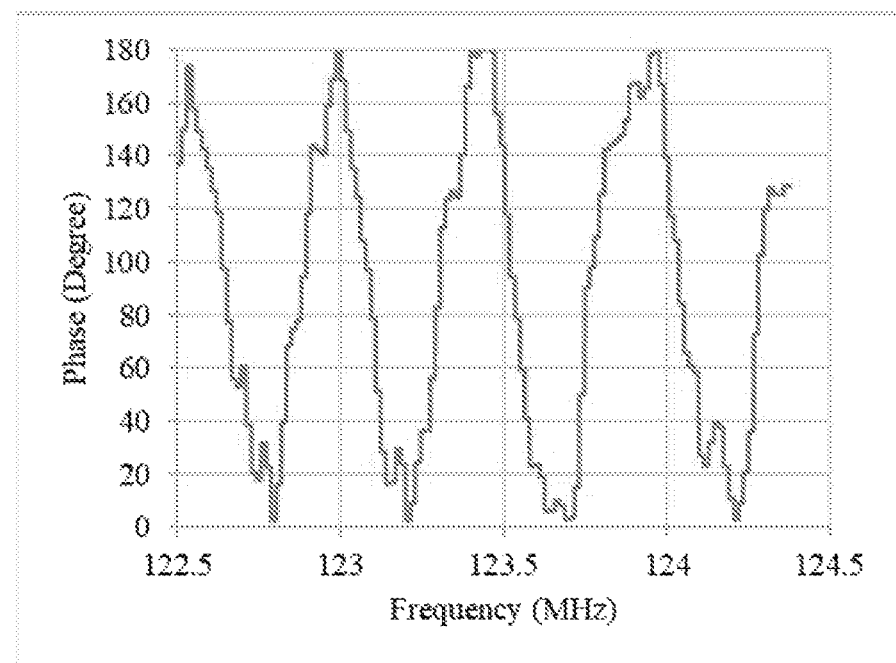
FIGS. 17A and 17B depict examples of a phase vs. frequency response of the system compared with vector network analyzer test results.
Figure 17B:
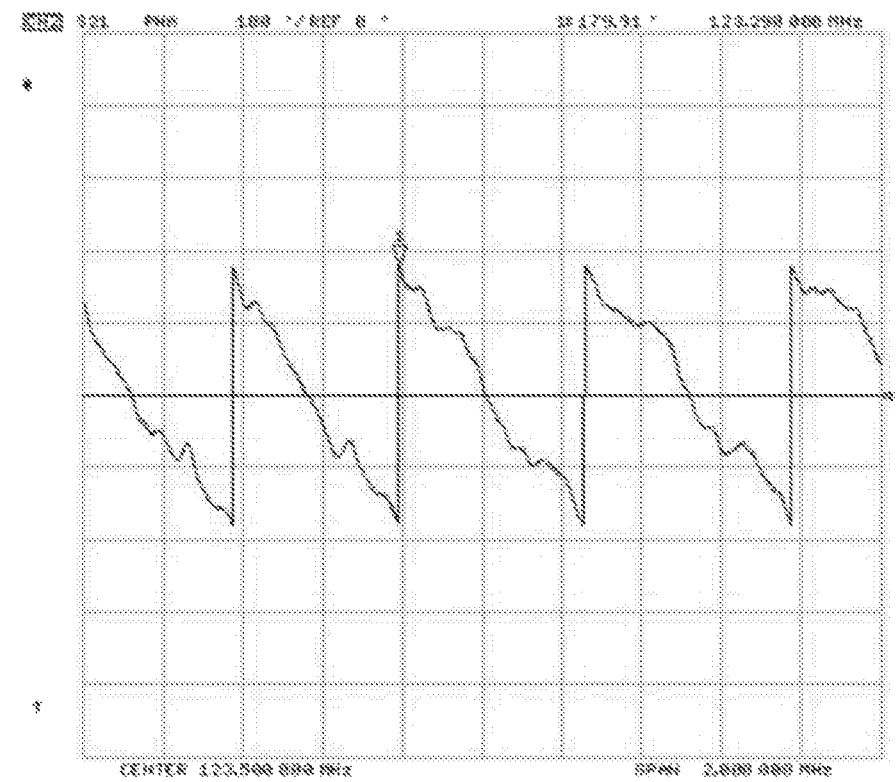

The system with a SAW device loaded was tested using frequency scanning mode and compared with the VNA results. The system was set under the network analyzer mode first, measuring the amplitude-frequency dependence. FIG. 12 shows the three times measurement results of the orthogonal SAW device and the S21 parameters of the same device measured by the VNA. The three measurements almost overlap one another in FIGS. 12A and 12C, showing the system can have high reliability and repeatability. The sensing channel can have an average center frequency of about 118.22 MHz, and the removal channel of about 77.66 MHz, which matches the VNA results, as shown in FIGS. 12A and 12D. The relative difference in amplitude could be caused by the systematic bias of amplifier and circuit wire, which is can be unimportant for sensing. The distorted frequency responses of VNA and prototype results could be due to the SU-8 O-ring cell on the top of the device surface. The phase vs. frequency comparison is excellent and is shown in FIGS. 17A and 17B.

The shift of the phase angle of the SAW device sensing path as a function of time can be sensitive to the loading on the surface. The system works in the sensing mode on the center frequency, which can be measured under the network analyzer mode before.

Figure 13:
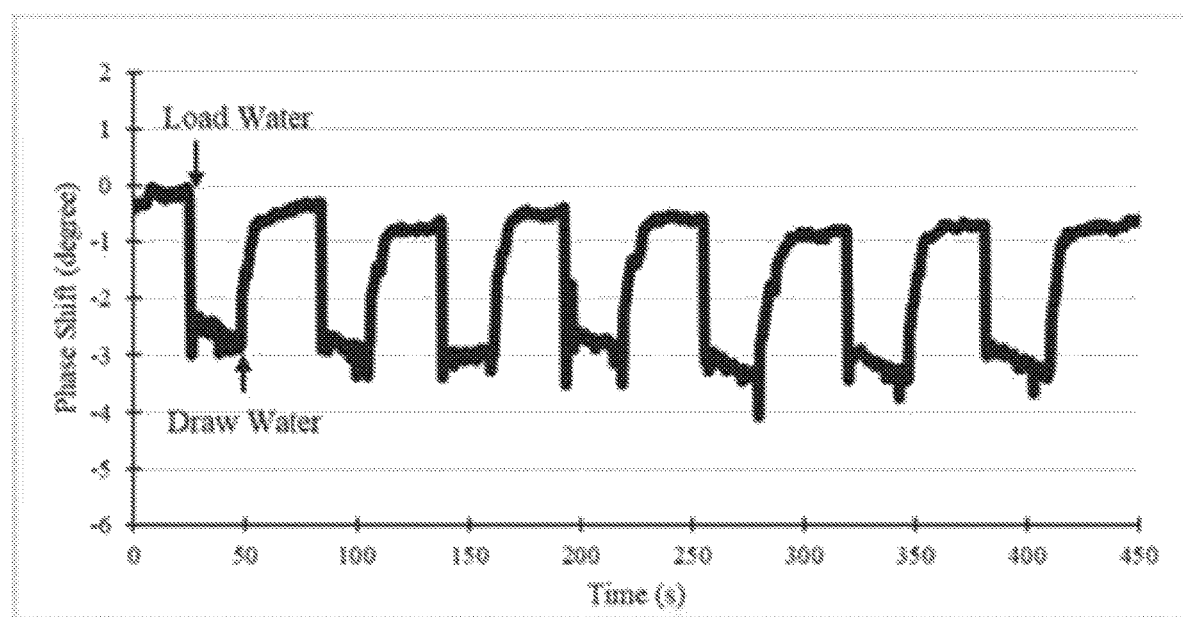
FIG. 13 depicts an example of a phase response of a surface acoustic wave device to a water drop loading and drawing.

The dynamic response of the system was tested by dropping water on the SAW sensor, as shown in FIG. 13. The baseline without liquid was measured first for 2 min. Once the system became stable, 10 µL of water was loaded in the O ring cell of SAW sensor (30 s), then, the water drop was drawn up using a pipette, after the data became stable again (60 s). This process was repeated several times to check the system repeatability.

As the result shows, the system can rapidly respond to the loading, with about 2.5° phase angle shift, and recovers to the initial level after drawing up the water and the surface is completely dry, indicating excellent system repeatability. The amplitude response was tested as well, and the device only has a very slight shift (less than 0.3 dB) after liquid loading, because the SH-SAW can have little energy consumption in liquid phase operation.

Rayleigh acoustic wave streaming can cause viscous heating of a liquid droplet on the surface of the SAW device. This heating could influence the sensing and can be a drawback during NSB removal. However, this heating effect can be rather weak with ST-quartz compared to other piezoelectric substrates such as 128° YX $LiNbO_3$. The ST-quartz device can be heated up by 0.7° C.

Figure 14:
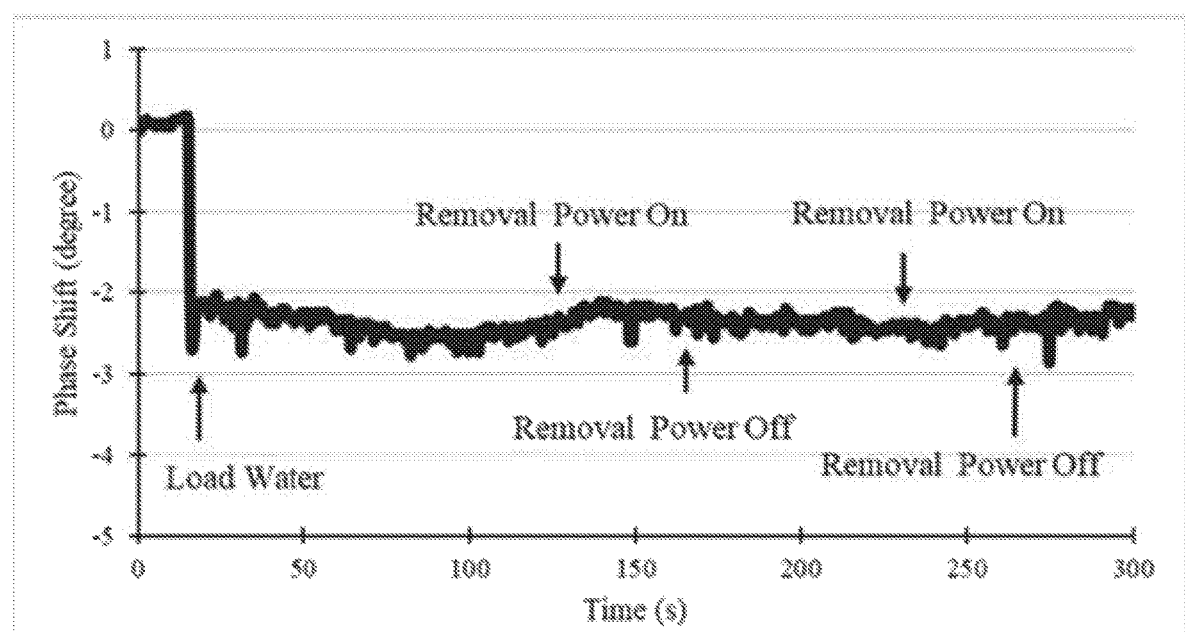
FIG. 14 depicts an example of a phase response of the surface acoustic wave device to the removal power switching on and off.

To evaluate its influence, the orthogonal chip can be tested with sensing and removal signal working simultaneously. First, the orthogonal SAW chip can be set working in sensing mode, and removal channel frequency can be set to its center frequency. Then, the phase shift can be monitored during the removal power being on and off. As shown in FIG. 14, the phase angle can become stable after the water was loaded (20 s). The removal power can be switched on at the moment of 120 s and then turned off after 60 s. After the moment of 240 s, this process can be repeated. Neither removal power on nor off would cause a significantly observable effect on the results of the sensing path.

Figure 15:
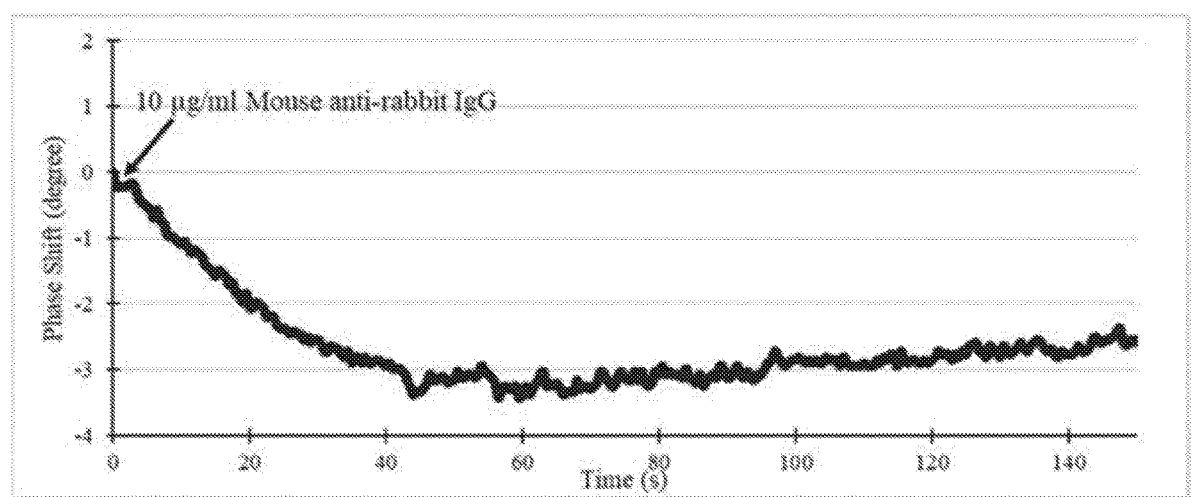
FIG. 15 depicts an example of a phase response of the surface acoustic wave device to mouse anti-rabbit IgG binding.

Preliminary biotesting was performed for general IgG detection. 10 µL mouse anti-rabbit IgG of 10 µg/mL was added on the modified SAW sensor and the phase shift was recorded as shown in FIG. 15. The IgG molecules assembling on the surface could result in phase decrease. After subtracting the PBS solution baseline change, the phase was significantly changed after the sample was added. It finally reached around 3° within 5 min, indicative of gradual binding on the sensor surface.

Figure 16A:
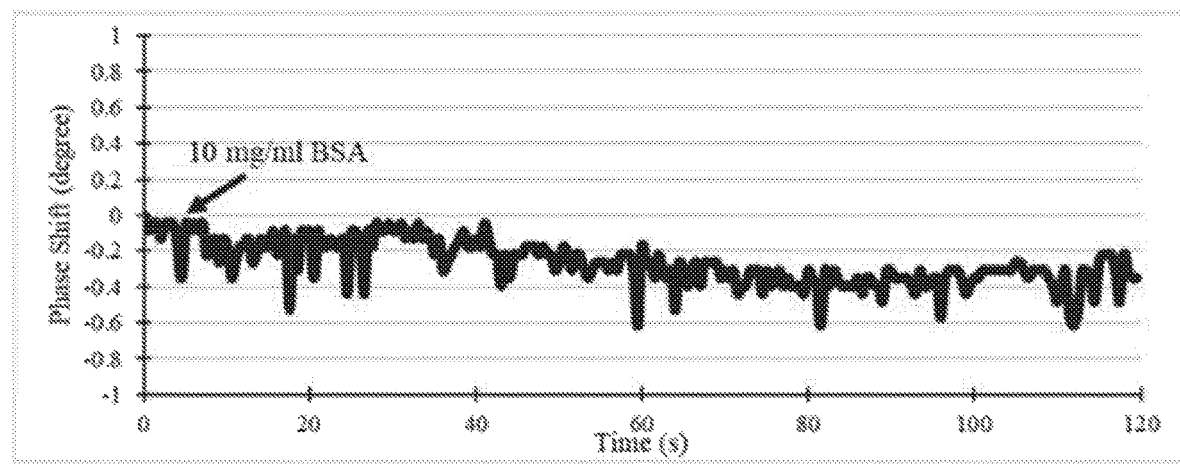
FIGS. 16A-16B depict examples of a phase response of a surface acoustic wave device to bovine serum albumin non-specifically bind on a surface and radio frequency power on and off for non-specific binding protein removal.
Figure 16B:
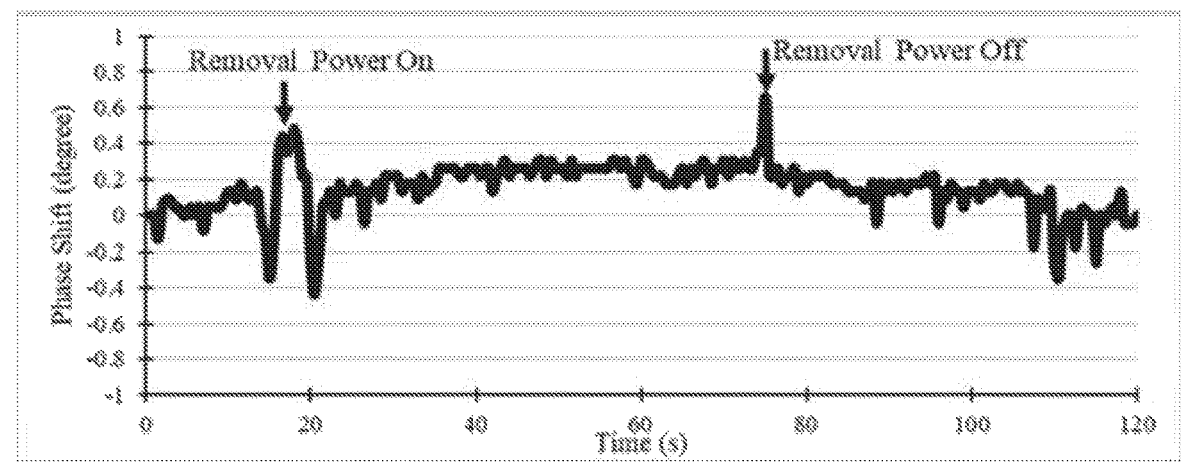

In addition, the NSB removal feature of this orthogonal SAW sensor was evaluated by loading with BSA solution. 1 mg/mL BSA in PBS solution was utilized as NSB protein in this test, which was added on the modified SAW sensor. As shown in FIG. 16A, a slight phase shift about 0.4° was detected, owing to the adsorption on the sensing surface within 120 s. This adsorption force was not strong enough to hold the BSA particles once the removal SAW streaming force was turned on. As indicated in FIG. 16B, after the removal power was turned on (15 s), the non-specifically bounded BSA molecules left the sensor surface resulting in a phase increase. The phase recovered to the initial level corresponding to the mass adsorbing after the removal power was switched off (75 s). A perturbation was observed when the removal streaming was switched on/off, which could be a result from the thick BSA solution exhibiting non-Newtonian flow behavior.

Disclosed herein is portable system for an orthogonal SAW sensor. This prototype can achieve biodetection and NSB removal in real-time measurements. The system has shown excellent performance in both phase and insertion loss testing. Such a portable system can have a significant advantage in integrating vector network analyzer and signal generator in a small size prototype, which implements a significant small, light-weight, low-cost, low-power detection instrument. Furthermore, this system can perform well for liquid biomolecule monitoring and has a great potential for point of care testing, with the indicated next step of the development of a biosensor for POC operation directly from body fluids such as blood and urine.

The invention claimed is:

1. A device for simultaneous sensing and nonspecific binding removal, comprising:
   a direct digital synthesizer configured to generate a radio frequency signal;
   an orthogonal surface acoustic wave circuit configured to receive a sensing input signal based on the radio frequency signal, receive a removal input signal based on the radio frequency signal, and generate a sensing output signal based on the sensing input signal and a removal output signal based on the removal input signal, the sensing output signal and the removal output signal being in orthogonal directions, the removal output signal configured to remove nonspecifically-bound protein on at least a portion of the device; and a detector configured to generate an output voltage based at least in part on the sensing input signal and the sensing output signal.

2. The device of claim 1, further comprising:
a radio frequency switcher configured to deliver the radio frequency signal into the sensing input signal and the removal input signal.

3. The device of claim 2, further comprising:
a digital gain amplifier configured to amplify the radio frequency signal; and
a low pass filter configured to receive the amplified radio frequency signal and perform low-pass filtering of the amplified radio frequency signal to provide the filtered radio frequency signal to the radio frequency switcher.

4. The device of claim 1, wherein the orthogonal surface acoustic wave circuit comprises: a first set of transducers to produce the sensing output signal and a second set of transducers to produce the removal output signal.

5. The device of claim 4, further comprising:
a first splitter configured to separate the sensing input signal into a first sensing input signal and a second sensing input signal; and
a second splitter configured to separate the removal input signal into a first removal input signal and a second removal input signal.

6. The device of claim 5, wherein the detector is configured to compare the second sensing input signal with the sensing output signal to generate the output voltage.

7. The device of claim 5, wherein the first set of transducers comprises a first transducer configured to receive the first sensing input signal and a second transducer configured to produce the sensing output signal, and
wherein the second set of transducers comprises a third transducer configured to receive a first removal input signal and a fourth transducer configured to receive a second removal input signal.

8. The device of claim 1, wherein the removal output signal comprises a Raleigh wave for generating acoustic streaming forces for nonspecific binding protein removal.

9. The device of claim 8, wherein the sensing output signal comprises a shear horizontal wave orthogonal to the Raleigh wave.

10. The device of claim 1, further comprising:
an oscillator configured to provide a stand frequency signal,
wherein the radio frequency signal is generated based on the stand frequency signal.

11. The device of claim 1, further comprising:
an analog-to-digital converter (ADC) configured to convert the output voltage to a voltage value; and
a microcontroller configured to receive the voltage value.

12. A method for simultaneous sensing and nonspecific binding removal, comprising:
generating, by a direct digital synthesizer, a radio frequency signal;
receiving, by an orthogonal surface acoustic wave circuit, a sensing input signal based on the radio frequency signal;
receiving, by the orthogonal surface acoustic wave circuit, a removal input signal based on the radio frequency signal;
generating, by the orthogonal surface acoustic wave circuit, a sensing output signal based on the sensing input signal and a removal output signal based on the removal input signal, the sensing output signal and the removal output signal being in orthogonal directions, the removal output signal configured to remove nonspecific binding; and
generating, by a detector, an output voltage based at least in part on the sensing input signal and the sensing output signal.

13. The method of claim 12, further comprising:
delivering, by a radio frequency switcher, the radio frequency signal into the sensing input signal and the removal input signal.

14. The method of claim 13, further comprising:
amplifying, by a digital gain amplifier, the radio frequency signal;
receiving, by a low pass filter, the amplified radio frequency signal;
performing, by the low pass filter, low-pass filtering of the amplified radio frequency signal; and
providing, by the low pass filter, the filtered radio frequency signal to the radio frequency switcher.

15. The method of claim 12, wherein the orthogonal surface acoustic wave circuit comprises: a first set of transducers to produce the sensing output signal and a second set of transducers to produce the removal output signal.

16. The method of claim 15, further comprising:
separating, by a first splitter, the sensing input signal into a first sensing input signal and a second sensing input signal; and
separating, by a second splitter, the removal input signal into a first removal input signal and a second removal input signal.

17. The method of claim 16, wherein the detector is configured to compare the second sensing input signal with the sensing output signal to generate the output voltage.

18. The method of claim 16, wherein the first set of transducers comprises a first transducer configured to receive the first sensing input signal and a second transducer configured to produce the sensing output signal, and
wherein the second set of transducers comprises a third transducer configured to receive a first removal input signal and a fourth transducer configured to receive a second removal input signal.

19. The method of claim 12, wherein the removal output signal comprises a Raleigh wave for generating acoustic streaming forces for nonspecific binding protein removal.

20. The method of claim 19, wherein the sensing output signal comprises a shear horizontal wave orthogonal to the Raleigh wave.

21. The method of claim 12, further comprising:
providing, by an oscillator, a stand frequency signal,
wherein the radio frequency signal is generated based on the stand frequency signal.

22. The method of claim 12, further comprising:
converting, by an analog-to-digital converter (ADC), the output voltage to a voltage value; and
receiving, by a microcontroller, the voltage value.

* * * * *